(12) United States Patent
Culton, Sr.

(10) Patent No.: US 10,267,026 B2
(45) Date of Patent: Apr. 23, 2019

(54) PORTABLE BIDET DEVICE AND SYSTEM

(71) Applicant: Steven Edwards Culton, Sr., Paradise, CA (US)

(72) Inventor: Steven Edwards Culton, Sr., Paradise, CA (US)

( * ) Notice: Subject to any disclaimer, the term of this patent is extended or adjusted under 35 U.S.C. 154(b) by 0 days.

(21) Appl. No.: 15/711,407

(22) Filed: Sep. 21, 2017

(65) Prior Publication Data

US 2018/0010324 A1 Jan. 11, 2018

Related U.S. Application Data

(63) Continuation-in-part of application No. 14/800,129, filed on Jul. 15, 2015, now abandoned.

(60) Provisional application No. 61/999,035, filed on Jul. 16, 2014.

(51) Int. Cl.
| | |
|---|---|
| *A61M 3/02* | (2006.01) |
| *E03D 9/08* | (2006.01) |
| *A47K 7/08* | (2006.01) |
| *A61H 35/00* | (2006.01) |

(52) U.S. Cl.
CPC ............. *E03D 9/085* (2013.01); *A47K 7/08* (2013.01); *A61M 3/0262* (2013.01); *A61M 3/0279* (2013.01); *A61H 35/00* (2013.01); *A61M 2210/1067* (2013.01)

(58) Field of Classification Search
CPC ...................................................... E03D 9/08
USPC ...................................................... 4/443–448
See application file for complete search history.

(56) References Cited

U.S. PATENT DOCUMENTS

| | | | | |
|---|---|---|---|---|
| 1,609,125 A | | 11/1926 | Waldron | |
| 4,259,754 A | * | 4/1981 | Bader | E03D 9/085 4/420.4 |
| D343,447 S | | 1/1994 | Thaler et al. | |
| 5,335,855 A | * | 8/1994 | Borod | A47K 3/26 239/152 |
| 5,409,167 A | * | 4/1995 | Borod | A47K 3/26 222/333 |
| 6,752,792 B1 | * | 6/2004 | Robertson | A61M 3/0258 4/443 |
| 8,007,478 B2 | * | 8/2011 | Lu | A47K 7/08 604/279 |
| 8,281,423 B2 | * | 10/2012 | Taylor | A47K 7/08 4/420.4 |
| 2006/0150311 A1 | * | 7/2006 | Chang Chien | E03D 9/085 4/420.4 |

(Continued)

FOREIGN PATENT DOCUMENTS

| | | |
|---|---|---|
| GB | 2503352 A | 12/2013 |
| WO | 2012166426 A1 | 12/2012 |

*Primary Examiner* — Lori L Baker
(74) *Attorney, Agent, or Firm* — Olav M. Underdal; IDP Patent Services

(57) ABSTRACT

A portable bidet can include a bidet tank that can contain a liquid for personal washing, a hand pump, a bidet hose, a control valve with a control lever, an angulated wand that includes a bend with a re-angulation, a spray nozzle, such that the portable bidet can be used by a person sitting on a toilet, such that the angulated wand protrudes downward and rearward between legs of the person, such that the bend of the angulated wand directs the spray of the liquid towards a perineal-genital-anal area of the person. The liquid can include water, and optionally soap and a hemorrhoid treatment composition.

21 Claims, 4 Drawing Sheets

(56) References Cited

U.S. PATENT DOCUMENTS

| | | | | |
|---|---|---|---|---|
| 2008/0078847 A1* | 4/2008 | Lai | A47K 7/08 | 239/373 |
| 2013/0000029 A1* | 1/2013 | Slawinski | E03D 9/08 | 4/443 |
| 2013/0175363 A1* | 7/2013 | Dobias | B05B 15/62 | 239/308 |
| 2013/0326802 A1* | 12/2013 | Newbill | A47K 7/08 | 4/443 |
| 2014/0096316 A1* | 4/2014 | Wu | E03D 9/085 | 4/443 |
| 2014/0259352 A1* | 9/2014 | Jones | E03D 9/085 | 4/443 |

* cited by examiner

PORTABLE BIDET DEVICE AND SYSTEM

CROSS-REFERENCE TO RELATED APPLICATIONS

This U.S. Non-Provisional application is a Continuation-In-Part of U.S. Non-Provisional application Ser. No. 14/800,129, filed Jul. 15, 2015, which claims the benefit of U.S. Provisional Application No. 61/999,035, filed Jul. 16, 2014; both of which are included by reference herein in their entirety.

FIELD OF THE INVENTION

The present invention relates generally to the field of bidets, and more particularly to methods, systems, and devices for portable bidets.

BACKGROUND OF THE INVENTION

The use of bidet hygiene is broadly recognized, and more so in some cultures than others. Ancient cultures, including the Romans and the Incans Mayans, deployed significant resources to channel mountain streams into their communities for personal uses of fresh water, irrigate total crops, ornament fountains, facilitate the removal of sewage, and enable their bidets. Use of bidets in Europe and the Middle East is common to this day. In Europe, private homes, hostels and hotels are commonly equipped with bidets, often as a separate toilet bowl, typically positioned next to the primary use toilet.

Anal-genital pressure washing as opposed to hand-finger-paper wiping as a sanitary issue, has socially defined hygiene, cultures and religions. Absent or poor hand washing after toileting is a known means of spreading diseases which has been legislated by health safety codes and regulations internationally. For the disabled and handicapped, efficient, thorough hand-assist paper post-toiling hygiene is often compromised due to orthopedic, arthritic or neurological inability to stretch, grasp and reach. Disease and body tissue injuries/complications caused by inefficient toilet paper hygiene are common in this group.

As a technical issue, a multitude of bidets have been developed, patented, presented and marketed parallel with the available science of the time. As technology has developed to the present day, most bidets have become powered electrically, tapped into the residential or commercial water supply, and heated through secondary water heating apparatus; all of which eliminate the possibility of portability, thereby requiring the user to become home dependent Past attempts at developing a portable bidet typically remain affixed to the toilet bowl or wall with limited water volume and poor pressure spray delivery capability. Wash water directional selection or control application ability require the user to physically move about and adapt 'to the direction of the water spray. Portability is limited to the length of the fixed hose connection to the water supply. Their use in a commercial toilet stall is not possible without changing and adapting the in-house plumbing. Such hand-held bidets have limited volumes which typically require hand-held directional control while simultaneously hand-compressing the reservoir. Once the volume is depleted, wash hygiene capability is exhausted until it can be refilled.

Seniors are frequently self-sequestered due to their toilet inabilities and insecurities. Effects of aging, such as arthritic changes, joint complications, rotator-cuff failures, spinal pain, obesity, and/or range-of-motion debilities all compromise normal physical activities and habits of daily living, ultimately requiring consideration and adaptation. Senior assist devices are available, such as canes, wheelchairs, walkers, grasping devices, etc., all of which improve individuals' quality of life and mobility. As the adult population becomes older, physical assistance has become a matter of usability, portability and profitability, Although there are stationary bidet plumbing fixtures available, the user is obligated to remain in proximity to that device. Hotels and travel destinations are often asked regarding their toilet assist abilities. Where handicapped assist rooms may be available, bidet assist devices usually are not. Where disabled persons may successfully mount the commode, and effect bowel emptying, they are often not able to provide efficient and thorough hygiene to complete the task. It becomes a deeply personal issue, best avoided by self-limiting outside travel and remaining "close-to-home". That is, provided there is acceptable toilet hygiene ability at home. Those same physical complications, which limit the user in outside-the-home applications, exist inside-the-home as well.

As such, considering the foregoing, it may be appreciated that there continues to be a need for novel and improved devices and methods for a portable bidet device.

SUMMARY OF THE INVENTION

The foregoing needs are met, to at least a great extent, by the present invention, wherein in aspects of this invention, enhancements are provided to the existing model of bidets in order to facilitate portable use.

In an aspect, a portable bidet, can include:
a) a bidet tank, which can be configured to contain a liquid under a pressure;
b) a bidet hose;
c) a control valve with a control lever, such that the control valve is in fluid connection with the bidet tank via the bidet hose, such that the control lever can stop a fluid flow in the control valve from the bidet tank when the control lever is not depressed, and allow the fluid flow when the control lever is depressed; and
d) an angulated wand, which can include:
a hollow wand, which includes a bend in an outer portion of the hollow wand, such that the hollow wand is in fluid connection with the control valve; and
a spray nozzle, which connected to an outer end of the hollow wand, such that that the spray nozzle is in fluid connection with the hollow wand;
such that the spray nozzle emits a spray of the liquid when the control lever is depressed;
whereby the angulated wand can be used by a person sitting on a toilet, such that the angulated wand protrudes downward and rearward between legs of the person, such that the bend of the angulated wand directs the spray of the liquid towards a perineal-genital-anal area of the person.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
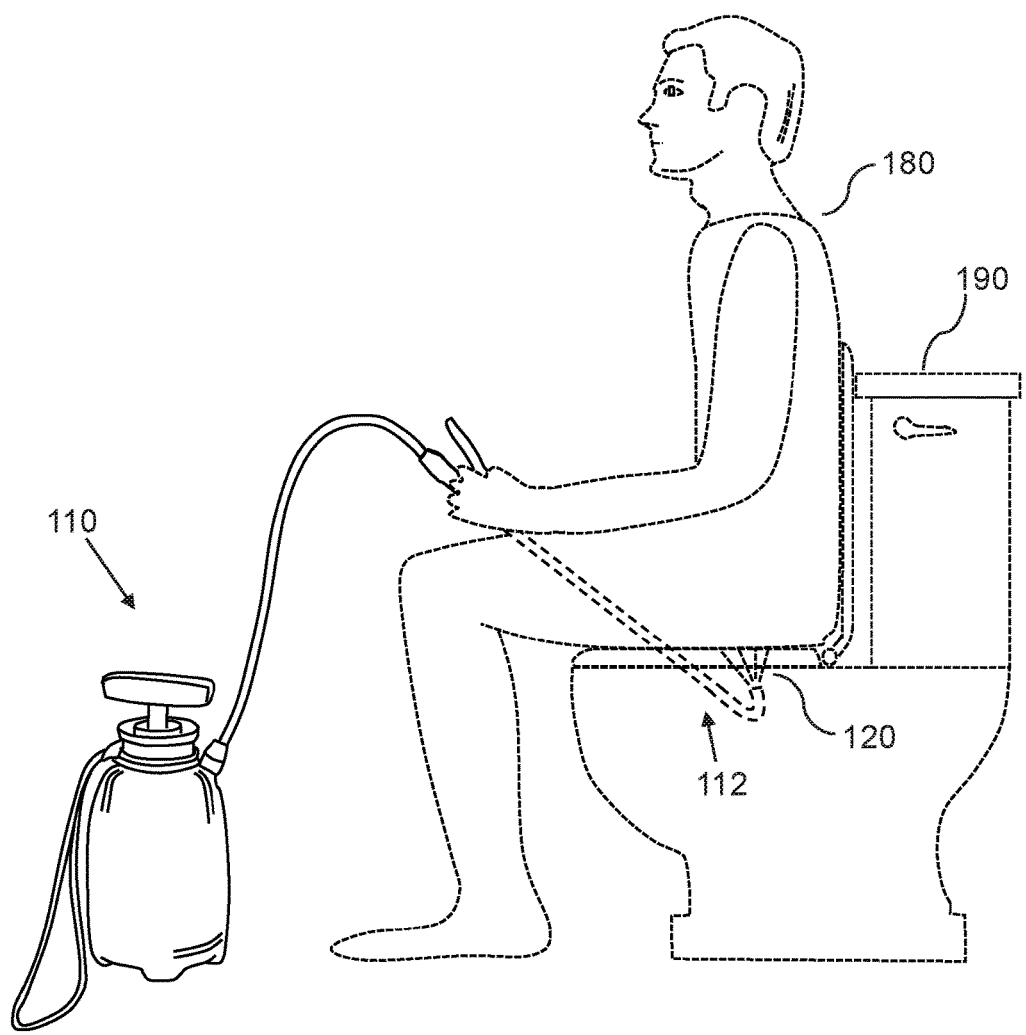
FIG. 1 is a perspective view of a portable bidet device in use, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a portable bidet 110 with reference to FIG. 1, in such manner that like reference numerals refer to like components throughout; a convention that we shall employ for the remainder of this specification.

In an embodiment, as shown in FIG. 1, a portable bidet 110 can be used as a bidet by a person 180 sitting on a toilet 190, such that an angulated wand 112 of the portable bidet 110 protrudes between the legs of the person 180.

Figure 2:
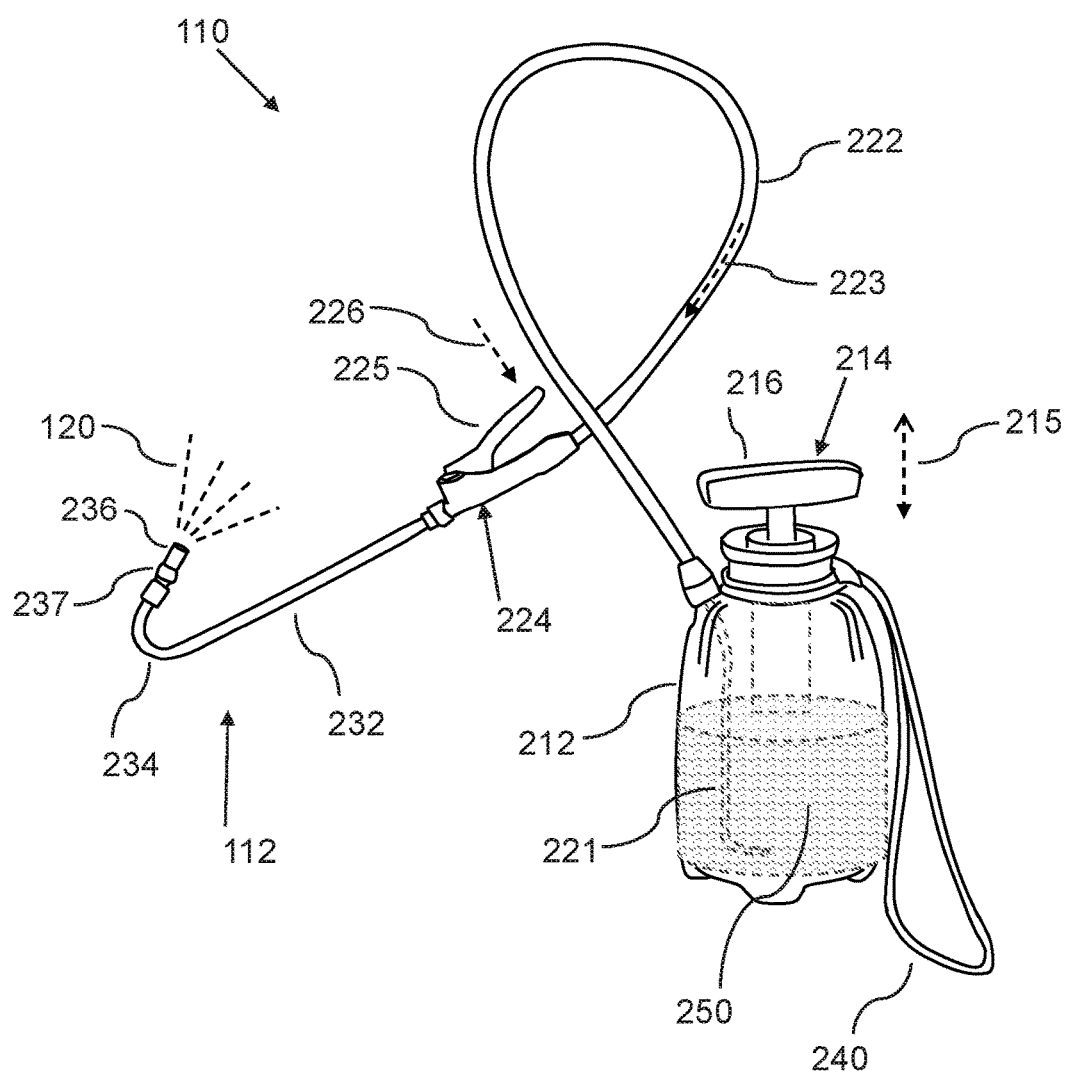
FIG. 2 is a perspective view of a portable bidet device, according to an embodiment of the invention.

In an embodiment, as shown in FIG. 2, a portable bidet 110 can include:
  a) a bidet tank 212, which can be a reservoir for storing a liquid 250 for personal washing, such as water, or water with soap or other detergent; such that the bidet tank 212 can further include:
    a hand pump 214, which can be configured to build up pressure in the bidet tank 212, via a pumping motion 215 of a handle 216 of the hand pump 214;
  b) a bidet hose 222;
  c) a control valve 224 including a control lever 225, which can also be a control button 225 or control switch 225, such that the control valve 224 is in fluid connection with the bidet tank 212 via the bidet hose 222, such that the control lever 225 is configured to stop a fluid flow 223 in the control valve 224 from the bidet tank 212 when the control lever 225 is not depressed, and to allow the fluid flow, i.e. open the control valve 224, when the control lever 225 is depressed 226, which can also be referred to as pressed in 226 or engaged 226; and
  d) an angulated wand 112, which can include:
    i. a hollow wand 232, which includes a bend 234, in a distal/outer portion of the hollow wand 232, such that the hollow wand 232 is j-shaped or substantially j-shaped, such that the hollow wand 232 is in fluid connection with the control valve 224; and
    ii. a spray nozzle 236, which connected to a distal/outer end of the hollow wand 232, such that that the spray nozzle is in fluid connection with the hollow wand 232, wherein the spray nozzle 236 can be configured to be adjustable with a finger screw 237 to adjust a volume and/or pattern of spray 120 of the liquid 250 from the bidet tank 212.
  such that the spray nozzle 236 emits a spray of the liquid 250 when the control lever 225 is depressed;
  whereby the angulated wand is configured to be used by a person sitting on a toilet, such that the angulated wand protrudes downward and rearward between legs of the person, such that the bend of the angulated wand directs the spray of the liquid towards a perineal-genital-anal area of the person.

Figure 3:
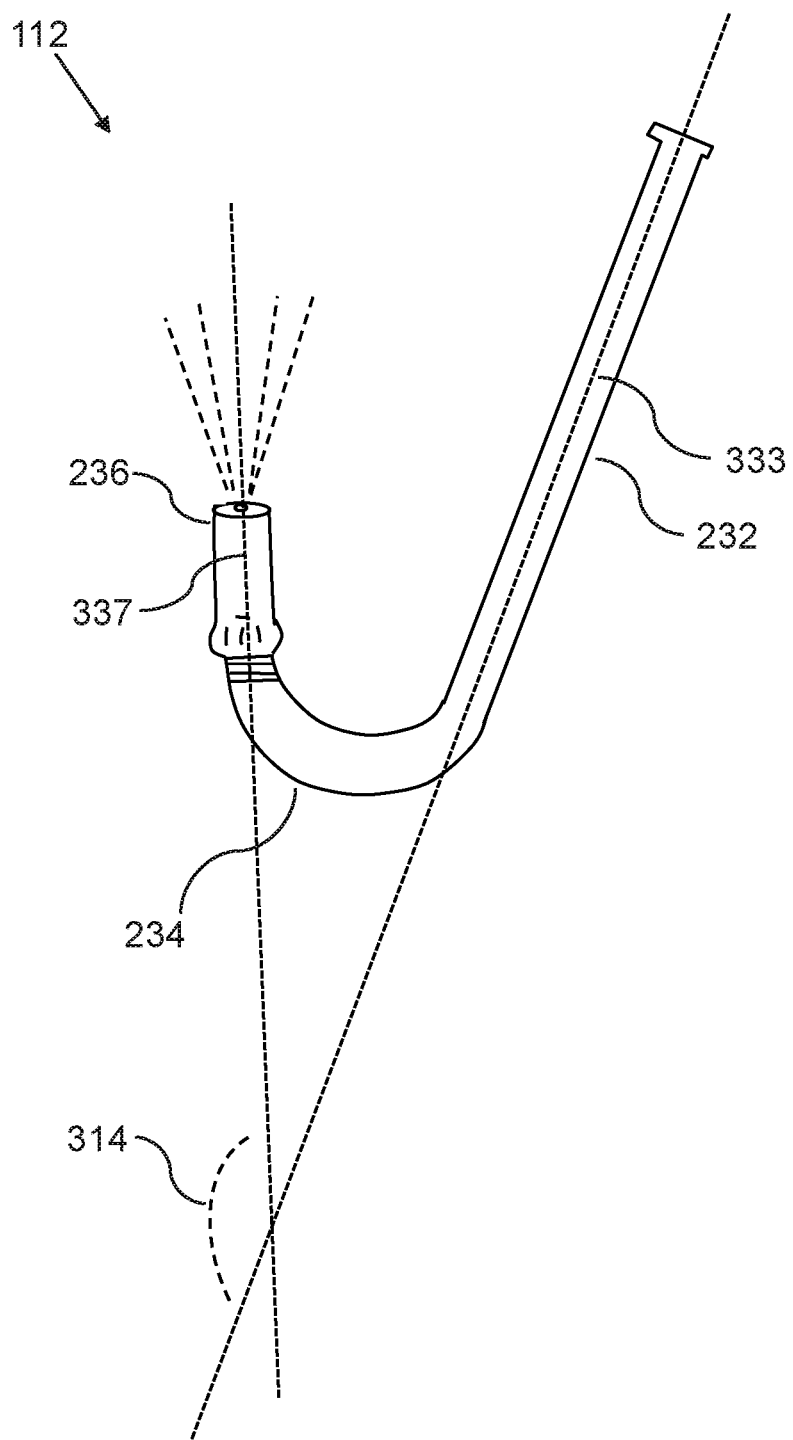
FIG. 3 is a side view of an angulated wand of a portable bidet device, according to an embodiment of the invention.

In a related embodiment, as shown in FIG. 3, the angulated wand 112 can be configured with a re-angulation 314, between an elongated direction 333 of the substantially straight inner/proximal portion of the angulated wand and a spray direction 337 of the spray nozzle 236, in a range of for example 90-180 degrees, 100-170, 110-170, 110-160, 120-160, or 120-155 degrees. In some embodiments, the re-angulation 314 can be substantially 135 degrees. The spray direction 337 can also be described as an elongated direction 337 of an outer/distal end of the hollow wand 232, when the spray direction of the spray nozzle 236 is parallel to (i.e. continues along) the elongated direction 337 of the outer/distal end of the hollow wand 232.

The re-angulation 314 measures how much the angulated wand 112 bends back from an elongated direction 333 of the substantially straight inner/proximal portion of the angulated wand 112. In a conventional spray canister, for example used for spraying insect spray, weed killer, house cleaning fluids, etc., the re-angulation will typically be substantially zero, i.e. for straight forward spraying, or at least less than 20-45 degrees. For such a conventional spray canister, the re-angulation 314 will never exceed 45 degrees, as this would risk spraying the liquid for application back onto the user.

In a related embodiment, the portable bidet 110 can further include:
  a lariat 240, which can be a cord mounted around an upper end of the bidet tank 212, such that the lariat 240 forms a loop, such that the lariat 240 is useful for attaching or hanging the portable bidet 110 from an attachment point.

In a further related embodiment, the lariat 240 can be removable, for example made of twenty-inch nylon cord, as a lariat, topped around the upper collar/end of the bidet tank 212, which allows a user 180 to suspend the device in a toilet stall, for example on the door latch, or coat hook; thus avoiding having to place the portable bidet 110 on the floor, for example in a public use toilet. The lariat 240 does not affect the portability of the device and is meant to be left in place, intact. The lariat 240 may be removed at the user's discretion with changing toileting environments.

In a related embodiment, the liquid 250 can further include a dissolved soap (i.e. a dissolved salt of a fatty acid, such as Sodium stearate, produced by saponification of oils or fats), including a soap solution, such as a liquid soap made for facial and/or hand use, and/or a dissolved soap gel, either of which can include an alcohol. The dissolved soap can be a water soluble surgical hand soap, in a liquid or gel formulation.

In a related embodiment, the liquid 250 can further include a hemorrhoid treatment composition, for alleviating discomfort from hemorrhoid, wherein the hemorrhoid treatment composition can include:
 a) Phenylephrine;
 b) Epinephrine;
 c) A corticosteroid, including Hydrocortisone;
 d) A Witch hazel extract;
 e) Pramoxine, also known as Pramocaine;
 f) Cinchocaine, also known as dibucaine;
 g) A composition of white petrolatum, glycerin, pramoxine and phenylephrine; for example in percentages by weight of the composition of: white petrolatum 15%, glycerin 14.4%, pramoxine hcl 1% and phenylephrine hcl 0.25%;
 h) A composition of cocoa butter, shark liver oil, and phenylephrine; for example in percentages by weight of the composition of: cocoa butter 85.5%, shark liver oil 3%, and phenylephrine hcl 0.25%;
 i) A composition of phenylephrine and witch hazel; for example in percentages by weight of the composition of: phenylephrine hcl 0.25% and witch hazel 50%; or
 j) Combinations thereof.

In a related embodiment, the liquid 250 can further include a therapeutic wash composition, similar to therapeutic or cosmetic mouthwash compositions, wherein the therapeutic wash composition can include at least one of:
 a) Cetylpyridinium chloride;
 b) Chlorhexidine;
 c) Essential oils, including essential oils of menthol (mint), thymol (thyme), methyl salicylate (wintergreen), eucalyptol (eucalyptus), and combinations thereof;
 d) Fluoride;
 e) Peroxide, including hydrogen peroxide; and
 f) Combinations thereof.

Figure 4:
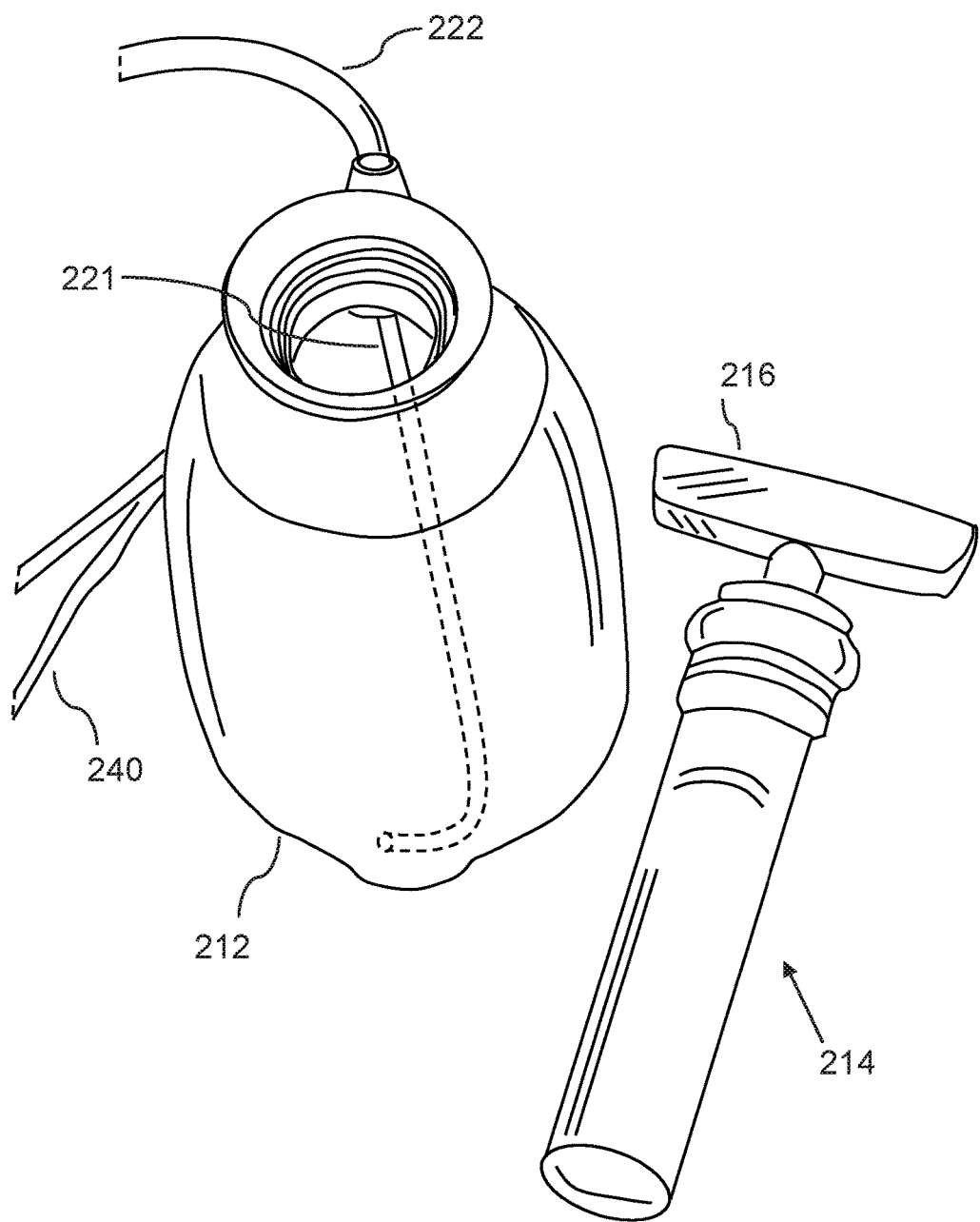
FIG. 4 is a perspective view of a bidet tank with the pump assembly screwed out, according to an embodiment of the invention.

In a related embodiment, as shown in FIG. 4, the hand pump 214, which can also be referred to as the pump assembly 214, can be removable and configured with a threading to screw into a threaded aperture of the bidet tank 212, such that the bidet tank 212 can be filled with the liquid 250, when the pump assembly 214 has been screwed out and removed from the bidet tank 212. FIG. 4 also shows the inner tube 221 which is connected to the bidet hose 222, such that the inner tube 221 is configured to reach to a bottom of the bidet tank 212 in order to allow the liquid 250 to flow from the bidet tank 212 under pressure created by the pump 214.

In related embodiments, the portable bidet 110 allows individual personal use, and is a portable, self-contained, refillable, reusable, manually pressurized, perineal-anal-genital washing device designed to replace or complement hand wiping with toilet paper.

In a related embodiment, the bidet tank 212 can be hand pumped to the desired water pressure level by the user 180.

In a related embodiment, while sitting on the toilet 190, the angulated wand 112 can be placed over the top of the toilet seat and down between the thighs underneath the buttocks in proximity to the perineum-anal-genital area. The generous length and flexibility of the bidet hose 222 allows the user to position the spray nozzle 236 exactly where hygiene is desired.

In a related embodiment, the finger screw 237 of the spray nozzle 236 may be turned clockwise or counterclockwise to adjust the intensity of the flow from gentle misting to direct flow.

In a related embodiment, the liquid 250 can be warm, tepid, or lukewarm, and can be water or any soothing hygienic liquid.

In a related embodiment, the bidet tank 212 can be configured with a 2-liter liquid volume, or in a range of 1-4 liters; and can be made from a hard plastic material.

In a related embodiment, the bidet hose 222 can be configured with a length of substantially 32 inches, or in a range of 24-40 inches; and can be a nylon-impregnated flexible plastic hose.

In a related embodiment, the angulated wand 112 can be configured with a length of substantially 13 inches, or in a range of 10-18 inches.

In related embodiment, the control valve 224, can also be described as a control valve assembly 224, which can include a handle to facilitate a user 180 in holding and directing the angulated wand 112.

In a related embodiment, the portable bidet 110 can further include:
 a pump 214, which can be mounted in the bidet tank or in the control valve assembly 224, or in some other position in the portable bidet 110 further comprises:
 such that the pump 214 is configured to build up the pressure in the bidet tank, or alternatively build up the fluid flow 223, in order to emit a spray 120 of the liquid 250. The pump 214 can for example be a hand pump 214, or a battery operated electric pump 214, such as used in some conventional designs for pesticide spray and weed control spray devices.

In another related embodiment, the control valve 224 can be in fluid connection between the bidet hose 222, and the hollow wand 232, such that the control lever 225 is configured to stop a fluid flow 223 in the control valve 224 from the bidet tank 212 when the control lever 225 is not depressed, and to allow the fluid flow 223 when the control lever 225 is depressed 226.

Here has thus been described a multitude of embodiments of the portable bidet 110, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A portable bidet, comprising:
 a) a bidet tank, which is configured to contain a liquid under a pressure;

b) a bidet hose;
c) a control valve with a control lever, such that the control valve is in fluid connection with the bidet tank via the bidet hose, such that the control lever is configured to stop a fluid flow in the control valve from the bidet tank when the control lever is not depressed, and to allow the fluid flow when the control lever is depressed; and
d) an angulated wand, comprising:
  a hollow wand, which comprises a bend in a distal portion of the hollow wand, such that the hollow wand is in fluid connection with the control valve; and
  a spray nozzle, which connected to a distal end of the hollow wand, such that that the spray nozzle is in fluid connection with the hollow wand;
wherein the bidet tank comprises the liquid that is contained inside the bidet tank, wherein the liquid comprises water;
wherein the liquid further comprises a hemorrhoid treatment composition;
wherein the hemorrhoid treatment composition, comprises phenylephrine;
such that the spray nozzle is configured to emit a spray of the liquid when the control lever is depressed;
whereby the angulated wand is configured to be used by a person sitting on a toilet, such that the angulated wand protrudes downward and rearward between legs of the person, such that the bend of the angulated wand directs the spray of the liquid towards a perineal-genital-anal area of the person.

2. The portable bidet of claim 1, where in the bidet tank further comprises:
  a hand pump with a handle, such that the hand pump is configured to build up the pressure in the bidet tank, via a pumping motion of the handle.

3. The portable bidet of claim 1, wherein the spray nozzle further comprises a finger screw, such that the spray nozzle is configured to be adjustable with the finger screw to adjust a volume and pattern of spray of the liquid from the bidet tank.

4. The portable bidet of claim 1, wherein the angulated wand is configured with a re-angulation, between an elongated direction of an inner portion of the angulated wand and a spray direction of the spray nozzle, in a range of 110-160 degrees.

5. The portable bidet of claim 4, wherein the re-angulation of the angulated wand is substantially 135 degrees.

6. The portable bidet of claim 1, further comprising:
  a lariat, which is a cord mounted around an upper end of the bidet tank, such that the lariat forms a loop.

7. The portable bidet of claim 1, wherein the liquid further comprises a dissolved soap.

8. The portable bidet of claim 1, wherein the hemorrhoid treatment composition, further comprises white petrolatum, glycerin, and pramoxine.

9. The portable bidet of claim 1, wherein the hemorrhoid treatment composition, further comprises cocoa butter and shark liver oil.

10. The portable bidet of claim 1, wherein the hemorrhoid treatment composition, further comprises witch hazel.

11. A portable bidet, comprising:
a) a bidet tank, which is configured to contain a liquid under a pressure;
b) a bidet hose; and
c) an angulated wand, comprising:
  a hollow wand, which comprises a bend in a distal portion of the hollow wand, such that the hollow wand is in fluid connection with the bidet hose; and
  a spray nozzle, which connected to a distal end of the hollow wand, such that that the spray nozzle is in fluid connection with the hollow wand;
wherein the bidet tank comprises the liquid that is contained inside the bidet tank, wherein the liquid comprises water;
wherein the liquid further comprises a hemorrhoid treatment composition, which comprises phenylephrine;
such that the spray nozzle is configured to emit a spray of the liquid;
whereby the angulated wand is configured to be used by a person sitting on a toilet, such that the angulated wand protrudes downward and rearward between legs of the person, such that the bend of the angulated wand directs the spray of the liquid towards a perineal-genital-anal area of the person.

12. The portable bidet of claim 11, where in the bidet tank further comprises:
  a pump, such that the pump is configured to build up the pressure in the bidet tank.

13. The portable bidet of claim 11, further comprising a control valve with a control lever, such that the control valve is in fluid connection between the bidet hose, and the hollow wand, such that the control lever is configured to stop a fluid flow in the control valve from the bidet tank when the control lever is not depressed, and to allow the fluid flow when the control lever is depressed.

14. The portable bidet of claim 11, wherein the angulated wand is configured with a re-angulation, between an elongated direction of an inner portion of the angulated wand and a spray direction of the spray nozzle, in a range of 110-160 degrees.

15. The portable bidet of claim 14, wherein the re-angulation of the angulated wand is substantially 135 degrees.

16. The portable bidet of claim 11, wherein the liquid further comprises a therapeutic wash composition, which is selected from the group consisting of:
  a) cetylpyridinium chloride;
  b) chlorhexidine;
  c) essential oils;
  d) fluoride;
  e) peroxide, including hydrogen peroxide; and
  f) combinations thereof.

17. A portable bidet, comprising:
a) a bidet tank, which is configured to contain a liquid under a pressure;
b) a bidet hose; and
c) an angulated wand, comprising:
  a hollow wand, which comprises a bend in a distal portion of the hollow wand, such that the hollow wand is in fluid connection with the bidet hose; and
  a spray nozzle, which connected to a distal end of the hollow wand, such that that the spray nozzle is in fluid connection with the hollow wand;
wherein the bidet tank comprises the liquid that is contained inside the bidet tank, wherein the liquid comprises water;
wherein the liquid further comprises a hemorrhoid treatment composition, which is selected from the group consisting of:
  phenylephrine;
  epinephrine;
  corticosteroid;

witch hazel;
pramoxine;
cinchocaine;
a composition of white petrolatum, glycerin, pramoxine and phenylephrine;
a composition of cocoa butter, shark liver oil, and phenylephrine;
a composition of phenylephrine and witch hazel; and combinations thereof;
such that the spray nozzle is configured to emit a spray of the liquid;
whereby the angulated wand is configured to be used by a person sitting on a toilet, such that the angulated wand protrudes downward and rearward between legs of the person, such that the bend of the angulated wand directs the spray of the liquid towards a perineal-genital-anal area of the person.

18. The portable bidet of claim 17, wherein the hemorrhoid treatment composition, comprises phenylephrine.

19. The portable bidet of claim 18, wherein the hemorrhoid treatment composition, further comprises white petrolatum, glycerin, and pramoxine.

20. The portable bidet of claim 18, wherein the hemorrhoid treatment composition, further comprises cocoa butter and shark liver oil.

21. The portable bidet of claim 18, wherein the hemorrhoid treatment composition, further comprises witch hazel.

* * * * *